(12) United States Patent
West et al.

(10) Patent No.: US 6,699,724 B1
(45) Date of Patent: Mar. 2, 2004

(54) METAL NANOSHELLS FOR BIOSENSING APPLICATIONS

(75) Inventors: Jennifer L. West, Pearland, TX (US); Nancy J. Halas, Houston, TX (US); Steven J. Oldenburg, Houston, TX (US); Richard D. Averitt, Los Alamos, NM (US)

(73) Assignee: Wm. Marsh Rice University, Houston, TX (US)

( * ) Notice: Subject to any disclaimer, the term of this patent is extended or adjusted under 35 U.S.C. 154(b) by 0 days.

(21) Appl. No.: 09/616,154

(22) Filed: Jul. 14, 2000

Related U.S. Application Data

(63) Continuation-in-part of application No. 09/038,377, filed on Mar. 11, 1998, now Pat. No. 6,344,272.
(60) Provisional application No. 60/144,136, filed on Jul. 16, 1999.

(51) Int. Cl.$^7$ ............................................. G01N 33/543
(52) U.S. Cl. ....................... 436/525; 436/518; 436/524; 435/7.1; 428/403
(58) Field of Search ................................ 436/518, 524, 436/525, 532, 808; 435/7.1, 7.92, 810; 428/402, 403; 252/478, 518, 520

(56) References Cited

U.S. PATENT DOCUMENTS

| | | | |
|---|---|---|---|
| 3,856,398 A | 12/1974 | Taylor | 355/64 |
| 4,099,854 A | 7/1978 | Decker et al. | 350/312 |
| 4,123,396 A | 10/1978 | Rembaum et al. | 526/24 |
| 4,313,734 A | 2/1982 | Leuvering | 23/230 |
| 4,416,998 A | 11/1983 | Adams et al. | 436/86 |
| 4,452,773 A | 6/1984 | Molday | 424/1.1 |
| 4,481,091 A | 11/1984 | Brus et al. | 204/157.1 |
| 4,624,923 A | 11/1986 | Margel | 435/176 |
| 4,877,647 A | 10/1989 | Klabunde | 427/123 |
| 4,979,821 A | 12/1990 | Schutt et al. | 356/246 |
| 5,023,139 A | 6/1991 | Birnboim et al. | 428/402 |
| 5,025,147 A | 6/1991 | Dürig et al. | 250/216 |
| 5,213,788 A | 5/1993 | Ranney | 424/9 |
| 5,213,895 A | 5/1993 | Hirai et al. | 428/403 |
| 5,249,077 A | 9/1993 | Laronga et al. | 359/385 |
| 5,266,498 A | 11/1993 | Tarcha et al. | 436/525 |
| 5,322,798 A | 6/1994 | Sadowski | 436/113 |
| 5,338,353 A | 8/1994 | Uchino et al. | 106/426 |
| 5,376,556 A | 12/1994 | Tarcha et al. | 436/525 |
| 5,427,767 A | 6/1995 | Kresse et al. | 424/9 |
| 5,445,972 A | 8/1995 | Tarcha et al. | 436/544 |
| 5,451,525 A | 9/1995 | Shenkin et al. | 436/63 |
| 5,479,024 A | 12/1995 | Hillner et al. | 250/458.1 |
| 5,501,949 A | 3/1996 | Marshall | 435/5 |
| 5,521,289 A | 5/1996 | Hainfeld et al. | 530/391.5 |
| 5,545,250 A | 8/1996 | Bergmann et al. | 75/252 |
| 5,552,086 A | 9/1996 | Siiman et al. | 252/408.1 |
| 5,567,628 A | 10/1996 | Tarcha et al. | 436/525 |
| 5,599,668 A | 2/1997 | Stimpson et al. | 435/6 |
| 5,779,976 A | 7/1998 | Leland et al. | 422/52 |
| 5,817,462 A | 10/1998 | Garini et al. | 435/6 |
| 5,845,083 A | 12/1998 | Hamadani et al. | 395/200.61 |
| 5,935,779 A | 8/1999 | Massey et al. | 435/6 |
| 5,938,617 A | 8/1999 | Vo-Dinh | 600/476 |
| 5,945,293 A | 8/1999 | Siiman et al. | 435/24 |
| 5,962,218 A | 10/1999 | Leland et al. | 435/6 |
| 5,990,479 A | 11/1999 | Weiss et al. | 250/307 |
| 6,078,782 A | 6/2000 | Leland et al. | 455/6 |
| 6,149,868 A | 11/2000 | Natan et al. | 422/82.05 |
| 6,156,173 A | * 12/2000 | Gotoh et al. | 204/403 |
| 6,180,415 B1 | 1/2001 | Schultz et al. | 436/518 |
| 6,344,272 B1 | * 2/2002 | Oldenburg | 428/403 |

FOREIGN PATENT DOCUMENTS

| | | | |
|---|---|---|---|
| WO | WO90/11890 | 10/1990 | |
| WO | WO97/40181 | 10/1997 | |
| WO | WO98/04740 | 2/1998 | ............ C12Q/1/68 |
| WO | WO98/33070 | 7/1998 | ......... G01N/33/543 |

OTHER PUBLICATIONS

M.M. Alvarez et al., *Optical Absorption Spectra of Nanocrystal Gold Molecules*, J. Phys. Chem. B (1997), vol. 101, pp. 3706–3712.

Bimboim, Meyer H., "Nonlinear Optical Properties of Structured Nanoparticle Composites", Mat. Res. Soc. Symp. Proc. vol. 164, 1990, pp. 277–282.

Nedelijkovic, Jovan, "Observation of Plasmon–Enhanced Optical Extinction in Silver–Coated Silver Bromide Nanoparticles", American Institute of Physics, Jun. 3, 1991, pp. 2461–2463.

Oldenburg, S.J., "Nanoengineering of Optical Resonances", Chemical Physics Letters 288 (1988), pp. 243–247.

Westcott, Sarah, "Formation and Adsorption of Clusters of Gold Nanoparticles onto Functionalized Silica Nanoparticle Surfaces", Langmuir, 1998, vol. 14, No. 19, pp. 5396–5401.

Zhou, H.S., "Controlled Synthesis and Quantum–Size Effect in Gold–Coated Nanoparticles", American Physical Society, 1994, vol. 50, No. 16, pp. 12 052–12 056.

(List continued on next page.)

Primary Examiner—Long V. Le
Assistant Examiner—Gary W. Counts
(74) Attorney, Agent, or Firm—Conley Rose, P.C.

(57) ABSTRACT

The present invention provides nanoshell particles ("nanoshells") for use in biosensing applications, along with their manner of making and methods of using the nanoshells for in vitro and in vivo detection of chemical and biological analytes, preferably by surface enhanced Raman light scattering. The preferred particles have a non-conducting core and a metal shell surrounding the core. For given core and shell materials, the ratio of the thickness (i.e., radius) of the core to the thickness of the metal shell is determinative of the wavelength of maximum absorbance of the particle. By controlling the relative core and shell thicknesses, biosensing metal nanoshells are fabricated which absorb light at any desired wavelength across the ultraviolet to infrared range of the electromagnetic spectrum. The surface of the particles are capable of inducing an enhanced SERS signal that is characteristic of an analyte of interest. In certain embodiments a biomolecule is conjugated to the metal shell and the SERS signal of a conformational change or a reaction product is detected.

25 Claims, 9 Drawing Sheets

OTHER PUBLICATIONS

Zhou, H.S., "Synthesis and Optical Properties of Coated Nanoparticle Composites", Jornal of Luminescence, 70, 1996, pp. 21–34.

R. D. Averitt, et al.; *Optical Properties and Growth Kinetics of Au coated au_2S Nanoshells*; Web Publication; Juan. 10, 1997; (1 p.).

S. J. Oldenburg, et al.; *Self–assembled Metal Shell Nanoparticles*; Web Publication; Jan. 10, 1997; (1 p.).

J. I. Steinfeld; *An Introduction to Modern Molecular Spectroscopy*; The MIT Press; Second Edition; Copyright©1974 and 1985; (8 p.).

P. F. Bernath; *Spectra of Atoms and Molecules*; Oxford University Press 1995; (8 p.).

R. D. Averitt, et al.; *Ultrafast Electron Dynamics in Gold Nanoshells*; The American Physical Society vol. 58, No. 16; 1998; (4 p.).

J. W. Haus, et al.; *Nonlinear–Optical Properties of Conductive Spheroidal Particle Composites*; Optical Society of America, vol. 6, No. 4, Apr. 1989; (pp. 797–807).

D. Stroud, et al.; *Decoupling Approximation for the Nonlinear–Optical Response of Composite Media*; Optical Society of America, vol. 6, No. 4, Apr. 1989; (pp. 778–786).

A. E. Neeves, et al.; *Composite Structures for the Enhancement of Nonlinear–Optical Susceptibility*; Optical Society of America; vol. 6, No. 4, Apr. 1989; (pp. 787–796).

P. Barnickel, et al.; *Silver Coated Latex Spheres*; Molecular Physics, 1989, vol. 67, No. 6; (pp. 1355–1372).

R. D. Averitt, et al.; *Plasmon Resonance Shifts of Au–Coated $Au_2S$ Nanoshells: Insight into Multicomponent Nanoparticle Growth*; Physical Review Letters, Jun. 2, 1997, vol. 78, No. 22; (pp. 4217–4220).

D. Sarkar, et al.; General Vector Basis Function Solution of Maxwell's Equations; *Physical Review, vol. 56, No. 1, Jul. 1997; (pp. 1102–1112)*.

Gregorakis, Alkibiades K. et al.; *Prostate–Specific Membrane Antigen: Current and Future Utility*; Seminars in Urologic Oncology, vol. 16, No. 1; Feb. 1998; pp.2–12.

Ozzello, L., et al.; *Conjugation of Interferon Alpha to a Humanized Monoclonal Antibody (HuBrE–3v1) Enhances the Selective Localization and Antitumor Effects of Interferon in Breast Cancer Xenografts*; Breast Cancer Research and Treatment 48: 1998; (pp. 135–147).

Bange, Johannes, ete al.; *Molecular Targets for Breast Cancer Therapy and Prevention*;; Nature Medicine; vol. 7, No. 5, May 2001; (pp. 548–552).

Vriesendorp, Huib M., et al.; *Radiolabeled Immunoglobulin Therapy in Patients with Hodgkin's Disease*; Cancer Biotherapy & Radiopharmaceuticals; vol. 15, No. 5, 2000; (pp. 431–445).

Chance, B., et al.; *Highly Sensitive Object Location in Tissue Models with Linear In–Phase and Anti–Phase Multi–Element Optical Arrays in One and Two Dimensions*; Proc. Natl. Acad. Sci. USA, vol. 90, Apr. 1993; (pp. 3423–3427).

Chen, Wei R. et al.; *Laser–Photosensitizer Assisted Immunotherapy: a Novel Modality for Cancer Treatment*; Cancer Letters 115 (1997) (pp. 25–30).

Chen, Wei R., et al.; *Photothermal Effects on Murine Mammary Tumors Using Indocyanine Green and an 808–nm Diode Laser; An in Vivo Efficacy Study*; Cancer Letters 98 (1996) (pp. 169–173).

Chen, Wei R., et al.; *Chromophore–Enhanced in Vivo tumor Cell Destruction Using an 808–nm Diode Laser*;; Cancer Letters 94 (1996) (pp. 125–131).

Chen, Wei R., et al.; *Chromophore–Enhanced laser–tumor Tissue Photothermal Interaction Using an 808–nm Diode Laser*; Cancer Letters 88 (1995) (pp. 15–19).

Jeong, B., et al.; *New Biodegradable Polymers for Injectable Drug Delivery Systems*; Journal of Controlled Release 62 (1999) (pp. 109–114).

Vrouenraets, Maarten B., et al.; *Development of meta–Tetrahydroxyphenylchlorin–Monoclonal Antibody Conjugates for Photoimmunotherapy*; Cancer Research 59; Apr. 1, 1999; (pp. 1505–1513).

Priest, John H., et al.; *Lower Critical Solution Temperatures of Aqueous Copolymers of N–Isopropylacrylamide and Other N–Substituted Acrylamides*; Chapter 18; Amer. Chem. Soc. 1987; (pp. 255–264).

Dong, Liang C., et al.; *Thermally Reversible Hydrogels*; Chapter 16; Amer. Chem. Soc. 1987; (pp. 236–244).

Eriksson, Cecilia, et al.; *The Initial Reactions of Graphite and Gold with Blood*; John Wiley & Sons, Inc.; 1997; (pp. 130–136).

Weissleder, Ralph, et al.; *In Vivo Imaging of Tumors with Protease–Activated Near–Infrared Fluorescent Probes*; Nature Biotechnology; vol. 17, Apr. 1999; (pp. 375–378).

Dong, Liang C., et al.; *Thermally Reversible Hydrogels: III. Immobilization of Enzymes for Feedback Reaction Control*; Elsevier Science Publishers B.V.; 1986; (pp. 223–227).

Yoshida, Ryo, et al.; *Modulating the Phase Transition Temperature and Thermosensitivity in N–Isopropylacrylamide Copolymer Gels*; J. Biomater. Sci. Polymer Edn., vol. 6, No. 6, 1994; (pp. 585–598).

Hoffman, Allan S., et al.; *Thermally Reversible Hydrogels: II. Delivery and Selective Removal of Substances from Aqueous Solutions*; Elsevier Science Publishers B.V.; 1986; (pp. 213–222).

Fisher, Anita M.R., et al.; *Clinical and Preclinical Photodynamic Therapy*; Lasers in Surgery and Medicine 17:2–31 (1995) Wiley–Liss, Inc.; (pp. 1–31).

R.D. Averitt, D. Sarkar, and N.J. Halas, "Plasmon Resonance Shifts of Au–Coated Au2S Nanoshells: Insight into Multicomponent Nanoparticle Growth," Phys. Rev. Lett 78, 4217–4220.

J. Oldenburg, S.L. Westcott, R.D. Averitt, and N. J. Halas, "Surface Enhanced Raman Scattering in the Near Infrared using Metal Nanoshell Substrates," Journal of the American Chemical Society, submitted (1998).

T.E. Rohr, Therese Cotton, Ni Fan, and P.J. Tarcha, "Immunoassay Employing Surface–Enhanced Raman Spectroscopy," Analytical Biochemistry 182, 388–398 (1989).

Luis M. Liz–Marzan, Michael Giersig, and Paul Mulvaney, "Synthesis of Nanosized Gold—Silica Core—Shell Particles,", Langmuir 1996, 12, 4329–4335.

S.J. Oldenburg, J.B. Jackson, S.L. Westcott, and N.J. Halas, "Infrared extinction properties of gold nanoshells", Applied Physics Letters, vol. 75, No. 19, pp. 2897–2899 (1999).

* cited by examiner

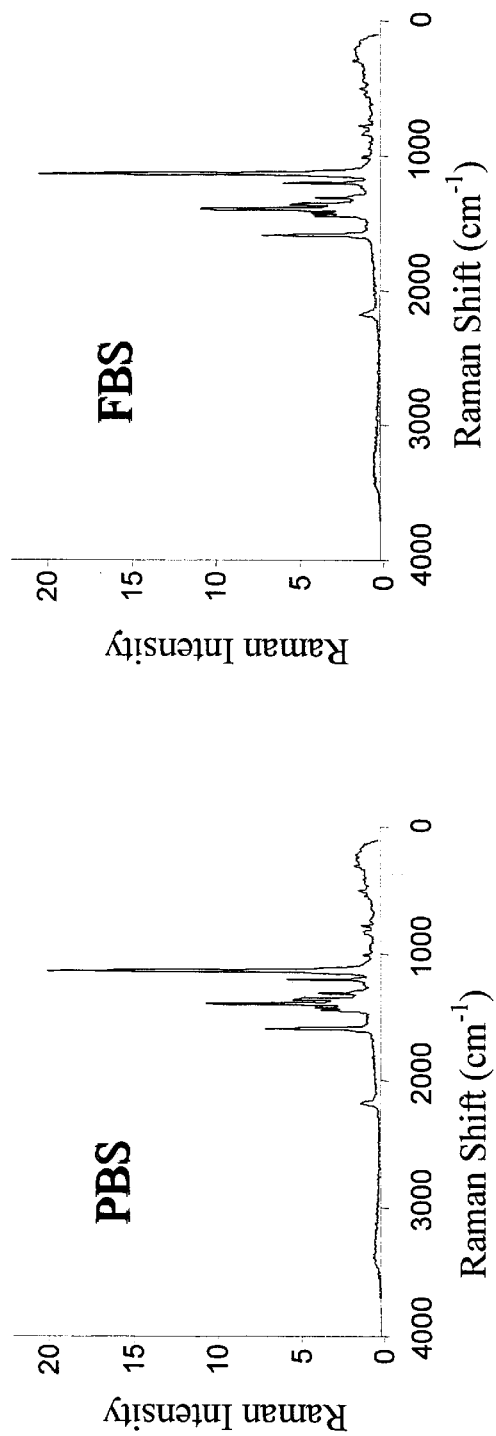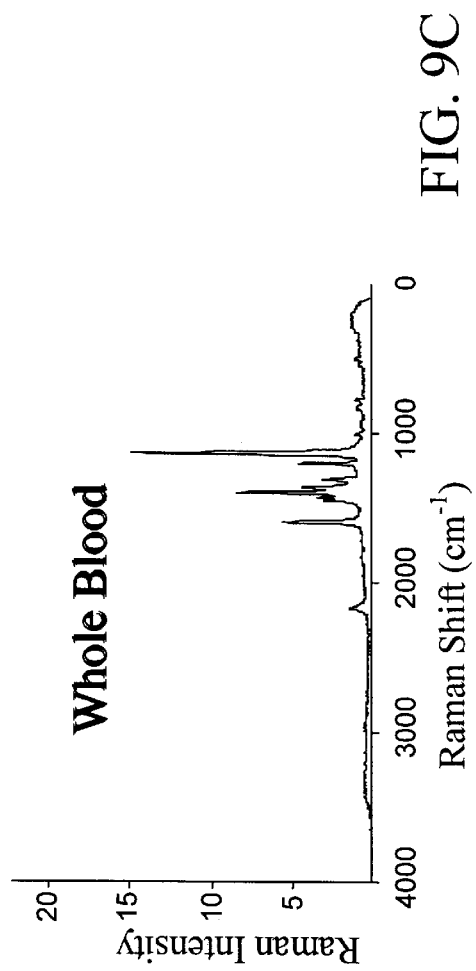
FIG. 9A
FIG. 9B
FIG. 9C

METAL NANOSHELLS FOR BIOSENSING APPLICATIONS

CROSS-REFERENCE TO RELATED APPLICATIONS

This application is a continuation-in-part of U.S. patent application Ser. No. 09/038,377 filed Mar. 11, 1998, now U.S. Pat. No. 6,344,272 and also claims the benefit of U.S. Provisional Application No. 60/144,136 filed Jul. 16, 1999. The disclosures of those applications are incorporated herein by reference.

STATEMENT REGARDING FEDERALLY SPONSORED RESEARCH OR DEVELOPMENT

This invention was made with government support under Grant No. N00014-97-1-0217 awarded by the Office of Naval Research and under Grant No. ECS-9258118 awarded by the National Science Foundation. The United States government has certain rights in the invention.

BACKGROUND OF THE INVENTION

1. Field of the Invention

The present invention generally relates to particles composed of a nonconducting core coated with a very thin metallic layer, and to methods of using these particles for sensing a chemical or biological analyte. More particularly, the invention relates to such particles having defined maximum absorption or scattering wavelengths, and, optionally, having one or more biomolecules conjugated to the metallic layer.

2. Description of Related Art

It has long been observed that an enormous enhancement of Raman scattering intensities is possible from many biologically significant organic molecules when they are adsorbed onto roughened silver electrodes or in a solution of aggregating colloid (Fleischmann, M. et al. *J. Chem. Soc. Commun.* 80 (1973); Duff, D. G., et al. *Langmuir* 9:2301 (1993)). This effect, known as surface enhanced Raman scattering (SERS), can yield a Raman spectrum as much as a million times stronger than the spectrum of the same molecule in solution. While this approach has been popular with Raman spectroscopy using visible excitation, SERS enhancement becomes almost a requirement when a near infrared excitation source is used, as in FT-Raman spectroscopy. Although infrared excitation eliminates sample fluorescence, it also results in marked decrease in sensitivity, further motivating the need for a sensitization method. Current methods being used for SERS enhancement of near infrared FT-Raman spectroscopy are frequently plagued by difficult substrate preparation, poor reproducibility, sensitivity to contamination, or limited suitability for in vivo use.

The SERS effect is primarily related to the field strength near the surface of the substrate upon illumination, whether the substrate is a roughened metal surface or an aggregate of metallic nanoparticles. The strongest field enhancement is obtainable at the plasmon resonance of the metal substrate or particle. It is for this reason that gold colloid (plasmon resonance=520 nm) is such an efficient SERS enhancer under visible Raman excitation (typically with an argon ion laser at 514 nm). This resonance coincides with the absorption maximum of hemoglobin (Gordy, E. et al. *J. Biol. Chem.* 227:285–299 (1957)), however, which significantly restricts the use of visible excitation Raman spectroscopy on biological systems.

The idea of exploiting SERS in biosensing applications has been pursued using other strategies for quite some time. Previous workers have used SERS to measure binding between biological molecules of mutual affinity, including antibody-antigen interactions (Rohr, T. E., et al. *Anal. Biochem.* 182:388–398 (1989)). The approach in that study included the use of an avidin-coated silver film as substrate and dye-antibody conjugates to optimally enhance the SERS effect. Although that method was used in a successful sandwich immunoassay, the use of a microscopic silver substrate and the necessity for conjugation of the biomolecules with specific (carcinogenic) chromophores for resonance Raman detection severely limits the adaptability of that approach.

U.S. Pat. No. 5,567,628 (Tarcha et al.) describes an immunoassay method for performing surface enhanced Raman spectroscopy. Various substrates are described, including solid particles of gold or silver. U.S. Pat. No. 5,869,346 (Xiaoming et al) describes an apparatus and method for measuring surface-sensitized Raman scattering by an antigen-antibody complex adsorbed to solid gold, silver or copper particles.

Optical glucose monitoring is one example of an extremely important and active field of research. The goal of this research is to provide a noninvasive method of monitoring and more optimally managing diabetes, a disease that affects millions of people worldwide. A variety of approaches are currently being pursued, including near- and mid-infrared spectroscopy, photoacoustic spectroscopy, polarimetry, diffuse light scattering, and Raman spectroscopy (Waynant, R. W., et al. *IEEE-LEOS Newsletter* 12:3–6 (1998)). In comparison to the other approaches in use, Raman spectroscopy with near infrared excitation offers the unique ability to discriminate between spectra from different analytes even when signals are small. Raman spectroscopy is the only all-optical technique currently under consideration in which the entire spectral signature of a chemical species can be obtained. The spectral signature is not obscured by water, and the significant penetration depth achieved with near-IR excitation (>1 mm) facilitates a variety of in vivo monitoring approaches. Raman spectroscopic measurements of glucose in human blood serum and ocular aqueous humor (using both conventional Raman and stimulated Raman gain spectroscopy) have also been reported (Wicksted, J. P., et al. *App. Spectroscopy* 49:987–993 (1995); and U.S. Pat. No. 5,243,983 issued to Tarr et al.). Since near infrared excitation results in a dramatic decrease in sensitivity relative to visible Raman excitation, the most outstanding current limitation to Raman-based glucose monitoring is the lack of sensitivity. This results in the necessity of long data collection times and multivariate analysis techniques for signal extraction.

The use of gold colloid in biological applications began in 1971, when Faulk and Taylor invented the immunogold staining procedure. Since that time, the labeling of targeting molecules, especially proteins, with gold nanoparticles has revolutionized the visualization of cellular or tissue components by electron microscopy (M. A. Hayat, ed. Colloidal Gold: Principles, Methods and Applications Academic Press, San Diego, Calif. 1989). The optical and electron beam contrast qualities of gold colloid have provided excellent detection qualities for such techniques as immunoblotting, flow cytometry and hybridization assays. Conjugation protocols exist for the labeling of a broad range of biomolecules with gold colloid, such as protein A, avidin, streptavidin, glucose oxidase, horseradish peroxidase and IgG (M. A. Kerr et al., eds. Immunochemistry Labfax BIOS Scientific Publishers, Ltd., Oxford, U.K. 1994).

Metal nanoshells are a new type of "nanoparticle" composed of a non-conducting, semiconductor or dielectric core coated with an ultrathin metallic layer. As more fully described in co-pending U.S. patent application Ser. No. 09/038,377, metal nanoshells manifest physical properties that are truly unique. For example, it has been discovered that metal nanoshells possess attractive optical properties similar to metal colloids, i.e., a strong optical absorption and an extremely large and fast third-order nonlinear optical (NLO) polarizability associated with their plasmon resonance. At resonance, dilute solutions of conventional gold colloid possess some of the strongest electronic NLO susceptibilities of any known substance. (Hache, F. et al. *App. Phys.* 47:347–357 (1988)) However, unlike simple metal colloids, the plasmon resonance frequency of metal nanoshells depends on the relative size of the nanoparticle core and the thickness of the metallic shell (Neeves, A. E. et al. *J. Opt. Soc. Am. B* 6:787 (1989); and Kreibig, U. et al. Optical Properties of Metal Clusters, Springer, N.Y. (1995)). The relative thickness or depth of each particle's constituent layers determines the wavelength of its absorption. Hence, by adjusting the relative core and shell thicknesses, and choice of materials, metal nanoshells can be fabricated that will absorb or scatter light at any wavelength across much of the ultraviolet, visible and infrared range of the electromagnetic spectrum. Whether the particle functions as an absorber or a scatterer of incident radiation depends on the ratio of the particle diameter to the wavelength of the incident light. What is highly desirable in the biomedical field are better, more sensitive devices and methods for performing in vivo sensing of chemical or biological analytes. Also desired are easier, more rapid and more sensitive methods and reagents for conducting in vitro assays for analytes such as autoantibodies, antiviral or antibacterial antibodies, serum protein antigens, cytokines, hormones, drugs, and the like.

SUMMARY OF THE INVENTION

Methods of in vitro and in vivo sensing of chemical or biochemical analytes employing SERS enhanced Raman spectroscopy are provided. Special metal coated particles ("metal nanoshells"), with or without conjugated biomolecules, and having diameters ranging from a few nanometers up to about 5 microns and defined wavelength absorbance or scattering maxima across the ultraviolet to infrared range of the electromagnetic spectrum are employed in the methods and compositions of the present invention.

One aspect of the invention provides a composition useful for biosensing applications. In certain embodiments, the composition comprises a plurality of particles and a support. In some embodiments the support comprises a medium such as a hydrogel matrix. In other embodiments the support comprises a substrate on which the particles are arrayed. Each particle comprises a non-conducting core having an independently defined radius and a metal shell adhering to the core and having an independently defined thickness. The terms "independently defined radius" and "independently defined thickness" mean that the desired thickness of each of the shell and core can be chosen and formed without dictating or requiring a certain thickness of the other. Each particle has a defined core radius:shell thickness ratio, a defined absorbance or scattering maximum wavelength (when measured in the same medium) in the ultraviolet to infrared range of the electromagnetic spectrum. The particle also has a surface capable of inducing surface enhanced Raman scattering, and, optionally one or more biomolecules conjugated to the particle surface. In some embodiments, a reporter molecule is conjugated to the shell or to the biomolecule. A reporter molecule could be an enzyme, a dye molecule, a Raman sensitive chemical, or the like. In some embodiments the conjugated biomolecule or the shell surface itself has an affinity for the analyte, causing at least some analyte molecules to adsorb or closely associate with the surface of the particle (e.g., localize within about 50–100 nm of the particle's surface, and preferably within about 10–20 nm of the surface). In some embodiments the support, or a portion of the support, has an affinity for the analyte sufficient to cause it to similarly localize near the surface of the particles. In certain preferred embodiments of the composition, the particles and the medium are in the form of a matrix such as a hydrogel that is permeable to an analyte of interest. Another aspect of the invention provides methods of making an optically tuned nanoshell especially for use in biosensing applications. The term "optically tuned nanoshell" means that the particle has been fabricated in such a way that it has a predetermined or defined shell thickness, a defined core thickness and core radius:shell thickness ratio, and that the wavelength at which the particle significantly, or preferably substantially maximally absorbs or scatters light is a desired, preselected value. For example, the selected wavelength of significant absorbance may correspond to an absorbance maximum (peak), or it may correspond to any strongly absorbed wavelength that falls on the "shoulder" of an absorbance peak, or the selected wavelength may fall within a strongly absorbing plateau region of the particle's absorbance spectral curve. It should be understood that the term "maximum absorbance" also includes this meaning, whenever the context applies. The particle's wavelength of significant absorbance may be chosen to substantially match a certain laser peak wavelength. A preferred embodiment of this method includes selecting the desired wavelength of light ($\lambda_{max}$) at which light of a selected wavelength will be significantly absorbed or scattered by the particle. A non-conducting core of radius $R_c$ is formed, and then a metal shell is grown or deposited onto the core, the final shell having a thickness $T_s$. This method also includes controlling the ratio of $R_c$:$T_s$ such that the wavelength of light maximally absorbed or scattered by the particle is approximately $\lambda_{max}$ in the UV to infrared range of the electromagnetic spectrum. In some embodiments, one or more analyte specific molecules, which may be a biomolecule such as an antibody, an antigen or an enzyme are conjugated to the shell. In certain embodiments a reporter molecule is instead or additionally conjugated to the shell or to the analyte specific molecule. The selected $\lambda_{max}$ preferably corresponds to the desired wavelength of the incident light that is to be employed when the nanoshells are used in a particular biosensing application.

Yet another aspect of the invention provides an in vitro method of assaying a biological analyte in a sample (e.g., blood, serum, or other body fluid). For example, the biological analyte could be a chemical or a biomolecule, such as proteins (e.g., antibodies, antigens and enzymes), peptides, oligonucleotides and polysaccharides, or a conjugate thereof.

According to certain embodiments, the in vitro assay method includes selecting one or more optically tuned nanoshells with an absorption or scattering maximum wavelength that substantially matches the wavelength of a desired source of electromagnetic radiation. In some embodiments the chosen nanoshells include one or more conjugated biomolecules. The method also includes associating the nanoshells with one or more molecules of the desired analyte contained in the sample such that an analyte/nanoshell complex is formed. In certain embodiments the method includes associating the nanoshells with a reporter molecule, in which case a reporter/analyte/nanoshell complex is formed. Either complex is capable of producing a Raman signal upon irradiation by the selected source. Preferably the source is in the near-IR range of the electromagnetic spectrum. The method further includes irradiating the complex with incident electromagnetic radiation at the predetermined wavelength so that surface enhanced Raman scattering is induced. A Raman scattering signal from the complex is detected and the signal is correlated to the presence and/or amount of the analyte in the biological sample. In preferred embodiments a SERS signal is also detected in the near-infrared range. A major advantage of the nanoshell biosensing technology of the present invention is that the need for indicator enzymes in many types of bioassays is obviated, which allows analysis of biological samples with little or no prior purification steps. Because a strong SERS signal from molecules right at the surface of the nanoshells can be obtained, other "contaminating" molecules in the unpurified or bulk sample, such as serum or whole blood, do not interfere with spectral response measurements of the molecule of interest.

In a further aspect of the present invention, a kit is provided for conducting nanoshell-based immunosorbent assays. These assays may be of the sandwich-type, direct- or indirect-types, analogous to the respective conventional immunosorbent assays. In one embodiment, the kit includes a quantity of a first antibody-nanoshell conjugate, and, optionally, a quantity of a control antigen having affinity for binding to the first antibody. This kit may also optionally include a quantity of a secondary antibody that has affinity for binding to an antigen-first antibody-nanoshell conjugate. In some embodiments a reporter molecule is bound to the second antibody. The nanoshells in the kit comprise a non-conducting core having an independently defined radius, a metal shell adhering to said core and having an independently defined thickness a defined core radius:shell thickness ratio, a defined absorbance wavelength maximum in the ultraviolet to infrared range, and a surface capable of inducing surface enhanced Raman scattering.

A further aspect of the present invention provides an in vivo method of monitoring a biological analyte. A preferred embodiment of this method comprises introducing a quantity of optically tuned metal nanoshell particles into a subject at a desired biosensing site in the body. In certain embodiments the site is internally accessible to an analyte of interest and is accessible to externally applied electromagnetic radiation. In other embodiments the site is accessible to the analyte and is also irradiated via an internally placed light source, as in a totally implantable system, for example. The particles are optically tuned such that the wavelength of light that is maximally absorbed or scattered by the particles substantially matches the wavelength of light emitted from a predetermined source of electromagnetic radiation in the ultraviolet to infrared range. For example, the average peak wavelength of a group of particles could be within about 10–15 nm of the 1064 nm wavelength of a Nd:Yag laser. Preferred embodiments of the method include selecting a source of electromagnetic radiation emitting light at a wavelength that matches said maximally absorbed or scattered wavelength. In certain embodiments the particles have an affinity for the analyte, and in some embodiments include a reporter molecule, which in certain embodiments contains a Raman active functional group. The method also includes externally applying radiation to the particles and any analyte molecules associated with the particles so that a SERS signal is produced. The method includes evaluating the signal and correlating a signal evaluation with the presence and/or amount of the analyte at the biosensing site.

Certain embodiments of the in vivo method of monitoring a biological analyte includes fabricating a quantity of optically tuned particles such that the wavelength of light that is maximally absorbed or scattered by said particles substantially matches the wavelength of light emitted from a predetermined source of ultraviolet-infrared electromagnetic radiation.

In accordance with still another aspect of the invention, a particle for biosensing applications is provided. The particle, also referred to as a metal nanoshell, comprises a non-conducting or dielectric core having an independently defined radius, a metal shell closely adhering to the core and having an independently defined thickness, and a defined core radius to shell thickness ratio. The particle also has a defined or predetermined wavelength absorbance or scattering maximum in the 300 nm to 20 $\mu$m range of the electromagnetic spectrum. In some embodiments the defined wavelength absorbance or scattering maximum is in the near-infrared range. In some embodiments, the maximum absorbance wavelength of the particle is set at about 800–1,300 nm or about 1,600–1,850 nm. In certain preferred embodiments, the particle has a wavelength maximum that substantially matches the peak wavelength of a given source of electromagnetic radiation and has a surface that is capable of inducing surface enhanced Raman scattering. In certain embodiments the metal shell has a surface with an affinity for associating analyte molecules.

In some embodiments of the particle of the invention, the particle has one or more analyte binding molecules conjugated to the metal shell surface. In certain embodiments the analyte binding molecule is a biomolecule, such as a protein, polypeptide, oligonucleotide or polysaccharide. In some embodiments the analyte binding molecule is a mixture of species of biomolecules conjugated to the shell. In certain embodiments the biomolecule is glucose oxidase and the analyte is glucose, and in certain other embodiments the biomolecule is an antibody and the analyte is a target antigen for the antibody. In certain preferred embodiments the shell comprises gold or silver, and the core comprises a material such as silicon dioxide, gold sulfide, titanium dioxide, polymethyl methacrylate (PMMA), polystyrene or a macromolecule such as a dendrimer. A preferred embodiment of the particle of the invention, especially suited for use in biosensing, has a gold shell and a silicon dioxide core. Other preferred nanoshells have a silver shell and a silicon dioxide core. The diameter of some of these particles is up to about 5 $\mu$m, with the core diameter being about 1 nm to nearly 5 $\mu$m, and the shell thickness being about 1–100 nm. In certain of the more preferred embodiments, the core is between 1 nm and 2 $\mu$m in diameter and the shell is less than 40 nm thick. In this embodiment, the shell is linked to the core through a linker molecule, and the particle has a wavelength of maximum absorbance or scattering between 300 nm and 20 $\mu$m. In some embodiments the particle is about 210 nm in diameter, has a core radius of about 100 nm, a shell thickness of about 10 nm, a core radius:shell thickness of about 10:1, and a maximum absorbance wavelength ($\lambda_{max}$) of about 1064 (SD±10 nm), substantially matching the 1064 nm (peak) Nd:YAG source as used in a FT-Raman laser spectrometer. Preferred embodiments of the particle of the invention have a gold shell or silver shell. Preferred embodiments of the particle have a core that comprises silicon dioxide, gold sulfide, titanium dioxide, polymethyl methacrylate (PMMA), polystyrene and macromolecules such as dendrimers. In another aspect of the invention, a chemical sensing device comprising certain of the above-described particles is provided. The chemical sensing device may be, for example, an all-optical sensor employing suitably designed nanoshells and SERS spectroscopy to detect and quantify a drug or a plasma protein such as a particular anti-viral or anti-bacterial antibody or a given cytokine.

Still other embodiments, features and advantages of the present invention will be apparent in the drawings and description that follows.

BRIEF DESCRIPTION OF THE DRAWINGS

FIG. 7A depicts a glucose sensor consisting of gold nanoshells (unfunctionalized) embedded in a glucose-permeable membrane or matrix. FIG. 7B depicts a glucose sensor consisting of glucose oxidase-nanoshell conjugates embedded in glucose permeable membrane.

FIG. 8A shows an antibody-nanoshell conjugate prior to assay. FIG. 8B shows an antibody-nanoshell conjugate after presentation to antigen analyte. FIG. 8C shows the nanoshell analog of the ELISA final sandwich immunoassay step, where, optionally, enzyme-linked antibodies are bound to the antigen-antibody complexes.

FIGS. 9A–C are graphs showing surface enhanced Raman scattering of dimethylaminoazobenzene labeled-IgG (DAB-IgG) conjugated nanoshells in biological samples. FIG. 9A shows Raman intensity vs Raman shift ($cm^{-1}$) for a sample of DAB-IgG conjugated nanoshells suspended in phosphate buffered saline (PBS). FIG. 9B is a similar graph for a sample suspended in fetal bovine serum (FBS), and FIG. 9C is a similar graph for a sample suspended in whole blood.

DETAILED DESCRIPTION OF PREFERRED EMBODIMENTS

Metal Nanoshells

The metal nanoshells fabricated as described in co-pending U.S. patent application Ser. No. 09/038,377 provide the functional structures that are the foundation of the preferred biosensing applications disclosed herein. Generally, assembly occurs by way of the following steps. First, core particles are grown or otherwise obtained. Next, a linker molecule is bound to the core. Then, clusters of molecules that comprise the conducting shell layer are reacted with a free reactive end on the linker molecules. These clusters may complete the shell layer or form nucleation sites for the growth of a complete shell layer around the core.

Generally, metal is deposited onto the tethered clusters and enlarges the clusters until a coherent metal shell of the desired thickness is formed. The metal can be deposited through reduction process of solution metal onto the tethered clusters. Alternatively, metal can be deposited on the tethered metal clusters by a "colloid-based" deposition process. The deposition can also be initiated or driven photochemically. The technique of depositing metal onto metal nucleation sites tethered to nonconducting core materials in solution is one of the novel features of the present methods.

The nanoshells employed for biosensing are preferably particles that range in diameter up to several microns, have a dielectric core, a metallic coating or shell, and a defined core radius:shell thickness ratio. Core diameters of the biosensing nanoshells range from about 1 nm to 4 $\mu$m or more, and shell thickness ranging from about 1 to 100 nm. For any given core and shell materials, the maximum absorbance or scattering wavelength of the particle depends upon the ratio of the thickness (i.e., radius) of the core to the thickness of the shell. Based on the core radius to shell thickness (core:shell) ratios that are achieved by the referenced synthesis method, nanoshells manifesting plasmon resonances extending from the visible region to approximately 5 $\mu$m in the infrared can be readily fabricated. The visible and near-infrared regions of the electromagnetic spectrum are of special interest for biological analysis or sensing applications.

By varying the conditions of the metal deposition reaction, the ratio of the thickness of the metal shell to the nonconducting inner layer can be varied in a predictable and controlled way. Particles can be constructed with metallic shell layer to core layer radius with ratios from 10 to $10^{-3}$. This large ratio range coupled with control over the core size results in a particle that has a large, frequency-agile absorbance over most of the visible and infrared regions of the spectrum.

Figure 1:
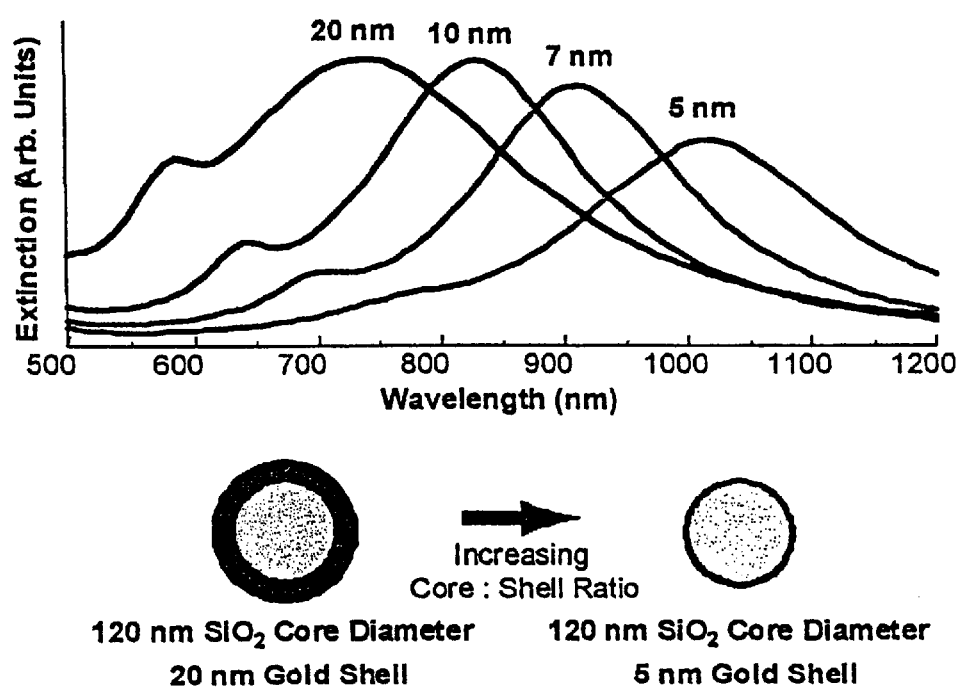
FIG. 1 is a graph showing calculated optical resonances of metal nanoshells having a silica core and a gold shell (suspended in water) over a range of core radius:shell thickness ratios.
Figure 2:
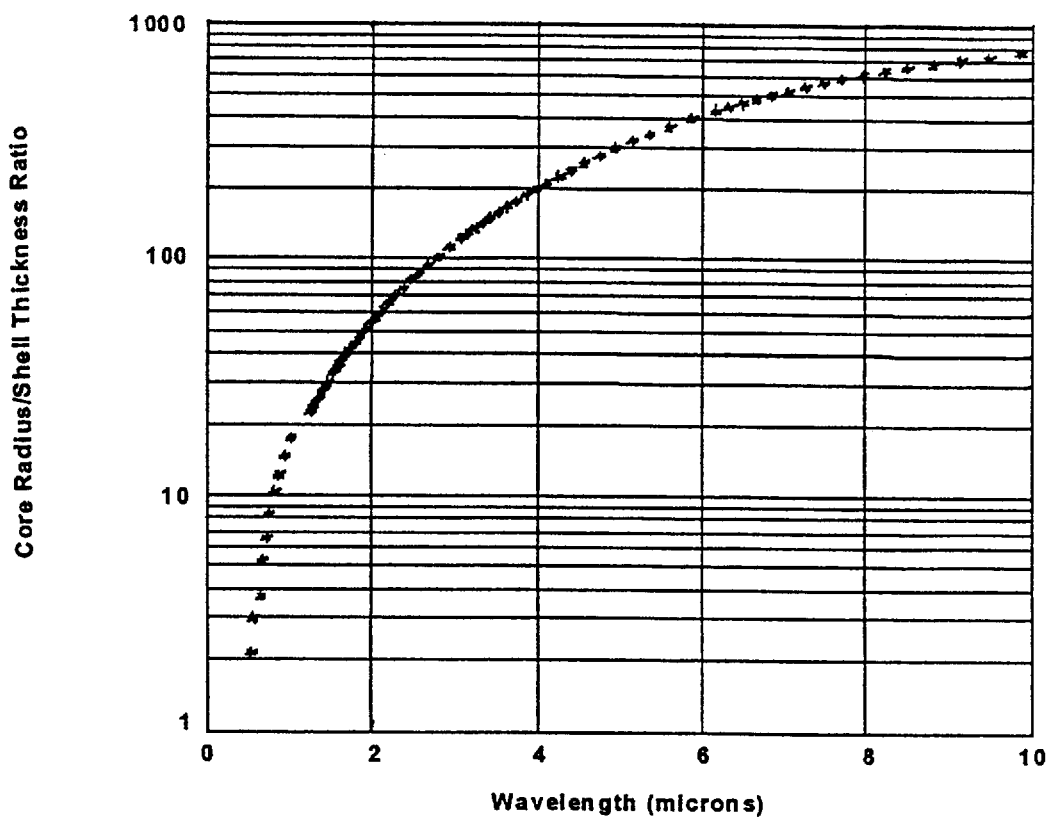
FIG. 2 is a graph showing calculated optical resonance wavelength versus the ratio of core radius to shell thickness for metal nanoshells having a silica core and gold shell (in water).

FIG. 1 shows calculated gold nanoshell plasmon resonances for particles of increasing core radius:shell thickness ratio. A Mie scattering calculation of the nanoshell plasmon resonance wavelength shift is depicted as a function of nanoshell composition for a nanoshell comprising gold layer deposited on a silica core. In this Figure, the core and shell of the nanoparticles are depicted to relative scale directly beneath their corresponding optical resonances. In FIG. 2, a plot of the core radius to shell thickness (core:shell) ratio versus resonance wavelength for a gold shell/silica core nanoparticle is displayed. By varying the conditions of the metal deposition reaction, the ratio of the thickness of the metal shell to the core radius is varied in a predictable and controlled way. Accordingly, particles can be constructed with core radius to shell thickness ratios ranging from about 2 to 1000. This large ratio range, coupled with control over the core size results in a particle that has a large, frequency-agile absorbance over most of the UV, visible and infrared regions of the spectrum.

By comparison, the shifts induced in the plasmon resonance of gold colloid by adsorption of molecular species are quite small, typically 10 nm or less. (Kreibig, U. et al. Optical Properties of Metal Clusters, Springer, N.Y. (1995)) The nonlinear optical (NLO) properties of metal nanoshells or nanoshells-constituent materials can be resonantly enhanced by judicious placement of the plasmon resonance at or near the optical wavelengths of interest. Thus, metal nanoshells demonstrate clear potential for optical device applications in the near infrared region, a wavelength range of critical technological importance. The agile "tunability" of the plasmon resonance is a property completely unique to metal nanoshells. In no other molecular or nanoparticle structure can the resonance of the optical absorption and NLO properties be systematically designed over such an extremely wide range of wavelengths.

Averitt, R. D. et al. (*Phys. Rev. Lett.* 78: 4217–4220 (1997)) investigated the optical properties of certain gold-terminated gold sulfide nanoparticles in detail. Quantitative agreement between the Mie scattering theory of FIG. 1 and the optical absorption in the $Au/Au_2S$ nanoparticles was achieved. As described in Ser. No. 09/038,377, a more generalized method for the growth of a uniform metallic layer of nanometer scale thickness onto a dielectric core has been developed. Also, see Oldenburg, S. J. et al. *Chem. Phys. Lett* 288:243–247 (1998). Briefly described, a preferred process includes growing or obtaining dielectric or semiconductor nanoparticles dispersed in solution. Very small (i.e., 1–2 nm) metal "seed" colloid is attached to the surface of the nanoparticles by molecular linkages. These seed colloids cover the dielectric nanoparticle surfaces with a discontinuous metal colloid layer. Additional metal is then grown onto the "seed" metal colloid adsorbates by chemical reduction in solution.

Figure 3:
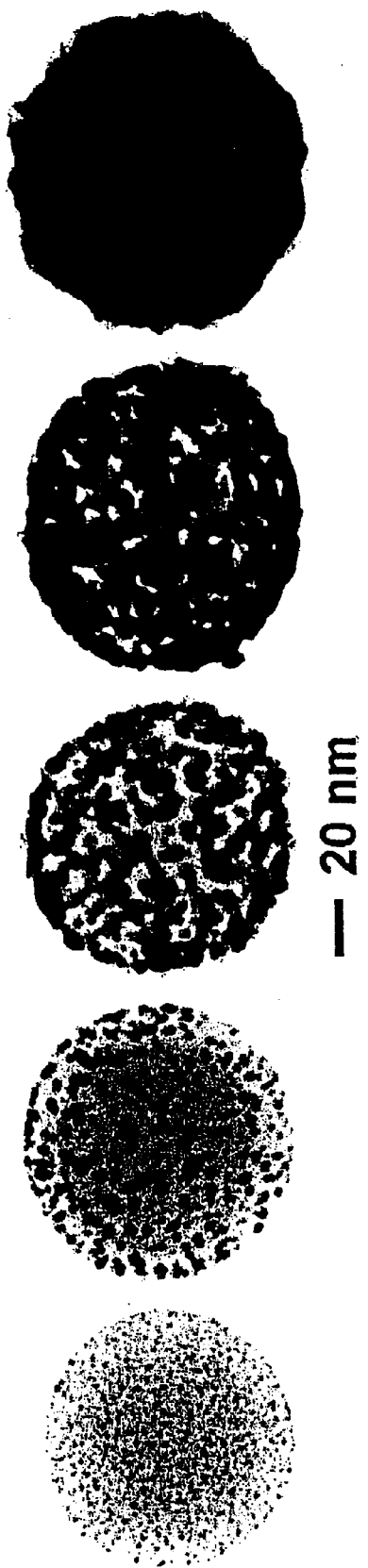
FIG. 3 depict transmission electron microscope images of silica core/gold shell nanoshells during shell growth.

This approach has been successfully used to grow both gold and silver metallic shells onto silica nanoparticles. Various stages in the growth of a gold metallic shell onto a functionalized silica nanoparticle are shown in FIG. 3. The term "functionalized" refers to a linker molecule and the gold colloid attached to the linker. FIG. 3 depicts transmission electron microscope images of silica core/gold shell nanoshells during shell growth. The relative length of 20 nm is shown below the images.

Figure 4A:
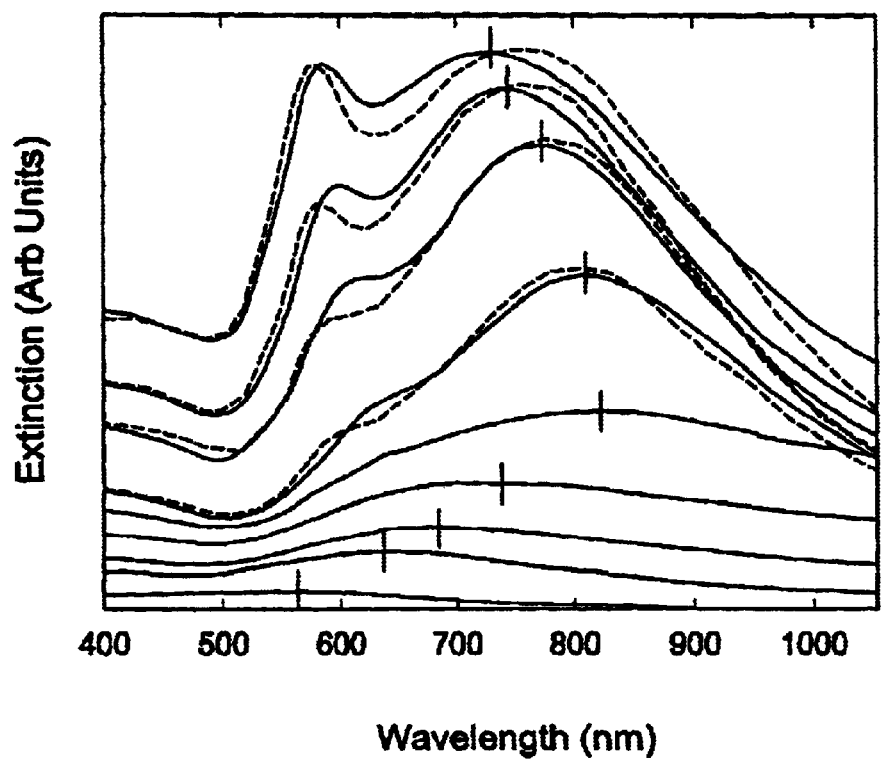
FIG. 4A is a graph showing growth of gold shells on 120 nm diameter silica nanoparticles.
Figure 4B:
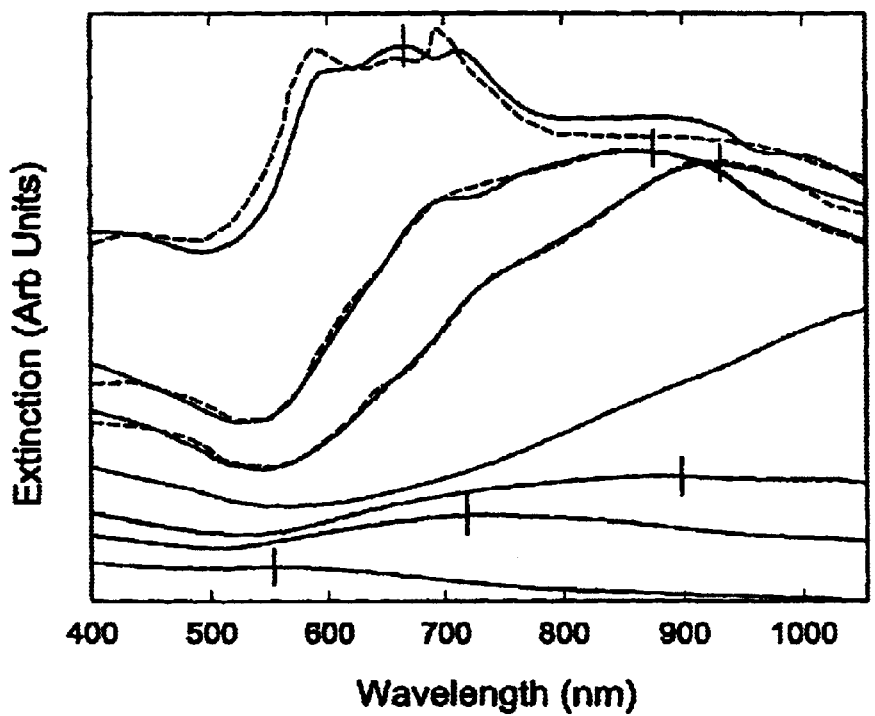
FIG. 4B is similar to FIG. 4A except that it shows the growth of gold shell on 340 nm silica particles.

FIGS. 4A–B are graphs showing the optical signature of nanoshell coalescence and growth for two different nanoshell core diameters. FIG. 4A shows growth of gold shell on 120 nm diameter silica nanoparticles. The lower spectral curves follow the evolution of the optical absorption as coalescence of the gold layer progresses. Once the shell is complete, the peak absorbance is shifted to shorter wavelengths. Specifically, the particles' absorbance maximum is related to the ratio of the thickness of the inner nonconducting layer to the thickness of the outer conducting layer. Corresponding theoretical peaks are plotted with dashed lines. FIG. 4B shows the growth of gold shell on 340 nm silica particles. Here the peak shifts are more pronounced, with only the shoulder of the middle curve visible in the range of the instrument employed in the test. Growth of metal nanoshells by this method takes just a few seconds and the yields obtained are greater than 98%. Nanoshells can be easily embedded into films or matrix materials and are stable in a wide range of organic and aqueous solvents.

Although in preferred embodiments the nanoshell particles are spherical in shape, the core may have other shapes such as cubic, cylindrical or hemispherical. Regardless of the geometry of the core, it is preferred that the particles be homogenous in size and shape in preferred embodiments. Preferably compositions comprising a plurality of metal nanoshells contain particles of substantially uniform diameter ranging up to several microns, depending upon the desired absorbance maximum of the particles. For example, monodisperse colloidal silica core particles can be produced by the base catalyzed reaction of tetraalkoxysilanes, by techniques known well to those of skill in the art. Alternatively, suitable silica particles are readily available from known commercial sources. Nearly spherical silica cores having sizes ranging from 10 nm to greater than 4 μm with a variation in particle diameter of only a few percent are preferred.

Suitable dielectric core materials include, but are not limited to, silicon dioxide, gold sulfide, titanium dioxide, polymethyl methacrylate (PMMA), polystyrene, and macromolecules such as dendrimers. The material of the non-conducting layer influences the properties of the particle. For example, if the dielectric constant of the shell layer is larger relative to a particle having a core with a given dielectric constant, the absorbance maximum of the particle will be blue-shifted relative to a particle having a core with a lower dielectric constant. The core may also be a combination or a layered combination of dielectric materials such as those listed above.

Suitable metals for forming the shell or outer layer include the noble and coinage metals, but other electrically conductive metals may also be employed, the particular choice depending upon the desired use. Metals that are particularly well suited for use in shells include but are not limited to gold, silver, copper, platinum, palladium, lead, iron or the like. Gold and silver are preferred. Alloys or non-homogenous mixtures of such metals may also be used. The shell layer is preferably about 1 to 100 nm thick and coats the outer surface of the core uniformly, or it may partially coat the core with atomic or molecular clusters.

EXAMPLE 1

Surface Enhanced Raman Scattering (SERS) Using Metal Nanoshells

Since metal nanoshells have a plasmon resonance that is designed into the particle by adjusting the particle core:shell ratio, their plasmon resonance can be shifted during growth of the shell to coincide with the excitation wavelengths of near infrared laser sources, such as the 1064 nm Nd:YAG source used in a FT-Raman laser spectrometer.

Figure 5:
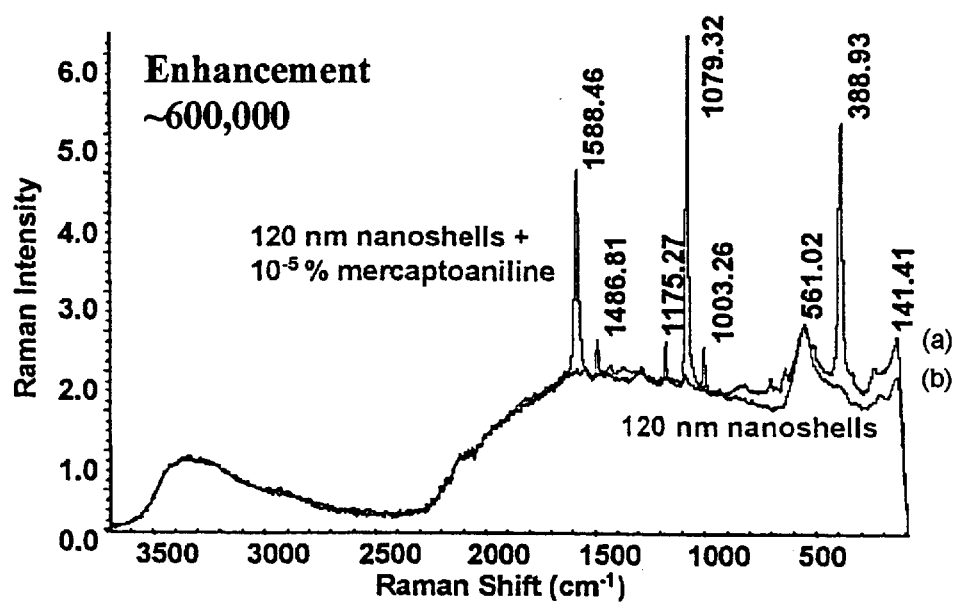
FIG. 5 is a graph showing SERS enhancement of mercaptoaniline with silica/gold nanoshells. The upper line (a) s the spectrum of 10–5% mercaptoaniline combined with the silica/gold nanoshells. The lower line (b) is the background Raman spectrum of the 120 nm diameter nanoshells only.

In a series of recent experiments, the SERS enhancement properties of metal nanoshells were investigated (Oldenburg, S. J. et al. *J. Chem. Phys.* 111:4729–4735 (1999), incorporated in its entirety herein by reference). The nanoshell plasmon resonance was placed at nominally 900 nm, so that the shoulder of the plasmon peak overlapped with the Raman excitation wavelength. FIG. 5 shows the SERS enhancement observed in this study for the molecule mercaptoaniline. An enhancement of 600,000 in the Raman signal was observed. In this case, the strong interaction between mercaptoaniline and the gold nanoshell surface results in a (likely covalent) binding of these molecules to the nanoparticle surfaces. The observed enhancement saturated at a mercaptoaniline concentration corresponding to monolayer coverage of the nanoshell surfaces, confirming that the Raman enhancement is indeed a local nanoparticle surface effect. In this study there was no contribution to the nanoshell SERS enhancement from nanoparticle aggregation, as no particle aggregation was detected. The observed SERS enhancement was due entirely to contributions from nonaggregated nanoshells dispersed in solution. It is advantageous to exploit this effect in biosensor design when possible. The metal nanoshells and conjugated nanoshells described herein provide a unique and wider array of SERS enhancing particles than the Au/Au$_2$S particles employed in that study.

EXAMPLE 2

Bioconjugation of Gold Nanoparticles/Nanoshells

Figure 6:
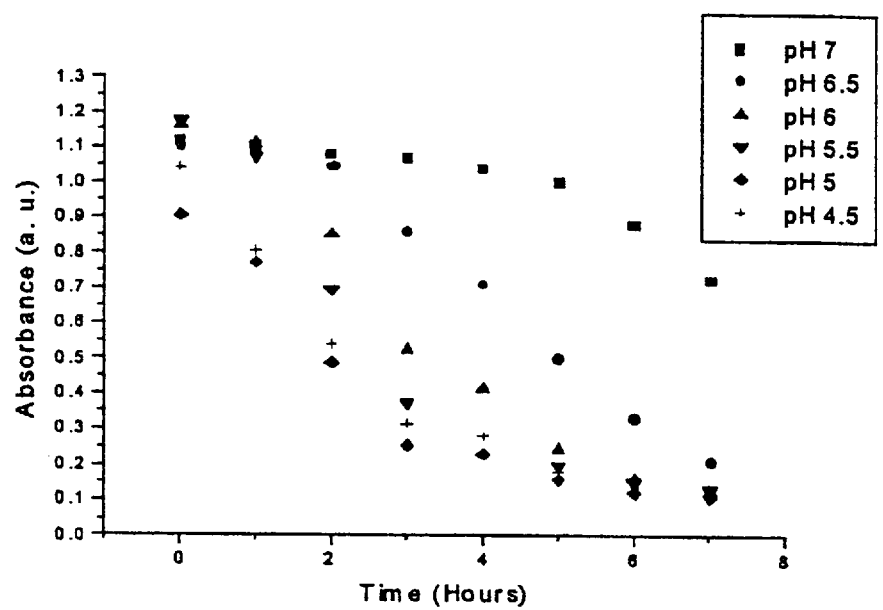
FIG. 6 is a graph showing glucose oxidase activity of GO-conjugated gold nanoshells over a 7 hr. period at pH 4.5 to 7.

Because the reduction of the outer metal layer of gold nanoshells is accomplished using the same chemical reaction as gold colloid synthesis, the surfaces of gold nanoshells are likely to be virtually chemically identical to the surfaces of the gold nanoparticles universally employed in conventional bioconjugate applications. Existing conjugation protocols for the labeling of a broad range of biomolecules with gold colloid (e.g., protein A, avidin, streptavidin, glucose oxidase, horseradish peroxidase and IgG) (M. A. Kerr et al., eds. Immunochemistry Labfax BIOS Scientific Publishers, Ltd., Oxford, U.K. 1994) will be directly repeatable or easily adaptable for use with gold nanoshells. Similar conjugation techniques are also expected to be readily adaptable for conjugation of nanoshells comprising other core materials. In one set of experiments, attachment of glucose oxidase (GO) to 150 nm diameter gold nanoshells was accomplished following a published protocol for gold colloid conjugation (Chen, X.-Y. et al. *Biochem. Biophys. Res. Comm.* 245:352–355 (1998)). Subsequently, the activity of the GO-nanoshell conjugate was monitored using conventional techniques. Attachment by adsorption proved successful over a range of pH values. Unlike parallel studies using citrate-stabilized gold colloid where pH-dependent flocculation occurred over the time span of several hours, no flocculation of the GO-nanoshell complex was observed over a time span of several days. Following repeated centrifugation, the activity of the GO-nanoshell complex was monitored in the presence of glucose solution using standard optical detection (Indigo Carmine-H$_2$O$_2$ redox pair). The relative pH-dependent activity of GO conjugated nanoshells is shown in FIG. 6. Other biomolecules may be conjugated to the metal nanoshells in a similar manner.

EXAMPLE 3

Gold Nanoshell-based Biosensors

A preferred biosensing strategy combines the enormous SERS enhancements provided by metal nanoshells with the facile bioconjugation capabilities of gold nanoshell surfaces. This combination provides a highly sensitive, high information density spectral probe suitable for monitoring specific biochemical processes of physiological importance. Visible light is not suitable for in vivo optical monitoring due to its absorption by hemoglobin. Ultraviolet light is also not suitable due to the potential for photochemical transformation of proteins and DNA. Raman scattering in the near infrared, enhanced by the gold nanoshell plasmon resonance, lacks these disadvantages and is predicted by the inventors to facilitate the same demonstrated SERS sensitivity in regions of high physiological transmissivity, such as the "water windows" of 800–1,300 nm and 1,600–1,850 nm (Anderson, R. R. et al. *J. Invest. Dermatol.* 77:13–19 (1981); and Duck. F. A., Physical Properties of Tissue: A Comprehensive Reference Book, Academic Press, San Diego, Calif. A (1990)). The core:shell ratio of the nanoshells is selected such that the desired absorption or scattering maximum corresponds to the desired incidence wavelength to be used in SERS spectroscopic measurement of a particular analyte. This design feature makes gold nanoshells uniquely suited as a microscopic biosensing substrate for all-optical in vitro and in vivo sensing applications. Using metal nanoshell resonant substrates to enhance the SERS signal eliminates the need for macroscopic metal substrates as well as resonance-conjugation of biomolecules for many SERS active analytes. However, biomolecules and/or reporter molecules may be conjugated to the nanoshell to enhance SERS detection and quantification, if desired.

It can be readily appreciated that the nanoshell particle diameter, the shell thickness, core thickness, and the core:shell ratio of the nanoshells may be selected in similar fashion such that a desired absorption maximum is obtained in the resulting nanoshells, and which corresponds to a desired wavelength for measuring a particular analyte in the ultraviolet, visible or near-infrared range of the electromagnetic spectrum.

EXAMPLE 4

All-optical in Vivo Glucose Sensing

Optical glucose sensing is aimed at providing a noninvasive way of monitoring blood glucose levels. Such a technique would be useful in managing diabetes, a disease that affects millions of people worldwide. In comparison to the other approaches in use today for in vivo glucose measurement, Raman spectroscopy with near infrared excitation offers the unique ability to discriminate between spectra from different analytes even when signals are small. Metal nanoshell-based glucose sensing overcomes the major limitation of existing Raman-based glucose monitoring systems by greatly improving the sensing sensitivity. The need for long data collection times and multivariate analysis techniques for signal extraction is obviated by employing nanoshell biosensors. Nanoshell based Raman glucose monitoring relies on the use of metal nanoshells to provide a strongly SERS-enhanced glucose signal under near infrared excitation. If desired, a glucose binding biomolecule and/or a SERS active reporter molecule may be conjugated to the nanoshell to enhance SERS detection and quantification. It is preferred to fabricate the shell and core thickness such that the plasmon resonance of the nanoshells matches the wavelength of the excitation laser used for SERS sensing. In this way a spectrum of the inelastically scattered light is obtained.

Figure 7A:
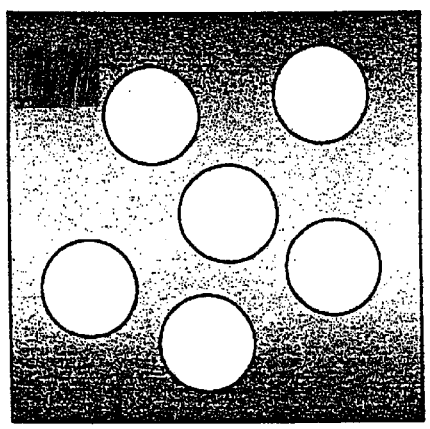
FIGS. 7A–B are conceptual illustrations of glucose sensing gold nanoshells.

Although glucose is described in the present example, it should be understood that any other biological analyte, particularly those that give a strong Raman signal, may be analyzed similarly. The glucose sensor shown in FIG. 7A includes nanoshells dispersed in a gel from which the glucose Raman signal of glucose molecules adjacent to the sensors can be directly monitored. One such glucose sensor comprises gold nanoshells (unconjugated) embedded in a glucose-permeable membrane or matrix, such as a hydrogel. The nanoshells are preferably fabricated with plasmon resonances corresponding to the Raman excitation laser wavelength. Embedding the nanoshells in a hydrogel matrix is often needed in order to reduce the immune response to the bioconjugate nanoshells and to prevent phagocytosis or migration of the nanoshells. A preferred hydrogel is formed from polyethylene glycol diacrylate (PEGDA), although other suitable hydrogel materials could be used instead. The suitability of a particular hydrogel can be evaluated by performing Raman studies on samples of hydrogel-embedded nanoshells to determine the sensitivity to the chemical species of interest. In this way the best performing candidate hydrogel matrices for a given application may be selected.

PEGDA is one material that has been shown to have excellent properties for in vivo use and to be highly permeable to glucose (Hill, R. S. et al. *Ann. N.Y. Acad. Sci* 831:332–343 (1997); and Quinn, C. P. et al. *Biomaterials* 16:389–396 (1995)). PEGDA hydrogels have been utilized in a number of biomaterials applications, including immunoisolation of glucose-responsive pancreatic islet cells and as a glucose-permeable coating for a redox-based glucose sensor. PEGDA hydrogels can be formed into thin coatings (2–100 $\mu$m) via a process called interfacial polymerization (Hill-West, J. L. et al. *Natl. Acad Sci. USA* 91:5967–5971 (1994)). This allows the creation of very thin, nanoshell-containing hydrogels subcutaneously in situ via an entirely injectable system. Following the injection-based implantation of the biosensing material, glucose monitoring is entirely noninvasive, assessed optically across the skin. Although preferred for many biosensing applications, it is not necessary in all applications to embed the nanoshells in a hydrogel in order to avoid migration of the biosensor particles or other problems. For example, the nanoshells could be deposited or arrayed on a thin film or some other type of implantable substrate.

Figure 7B:
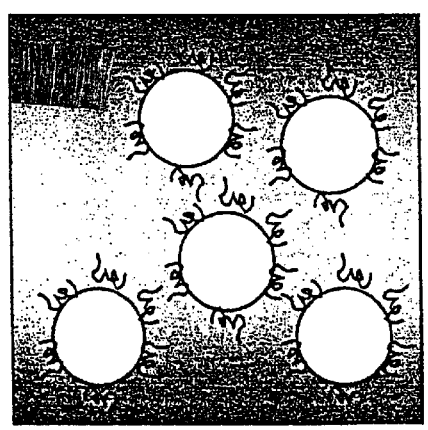

An alternative approach for using nanoshells in biosensing is shown conceptually in FIG. 7B, which depicts a glucose sensor consisting of functionalized nanoshells, e.g., glucose oxidase-nanoshell conjugates. The conjugated nanoshells are preferably embedded in a glucose permeable membrane, as described above. In this case, the metal nanoshells have been conjugated with the enzyme glucose oxidase prior to dispersal in a hydrogel, or hydrogel precursors, and implantation into a subject. In addition to the spectral signal of adjacent glucose molecules, a variety of other spectral features are available for optical monitoring. For example, conformational changes in glucose oxidase upon glucose binding, or the products of glucose oxidation, gluconic acid and $H_2O_2$ may be monitored. Because bioconjugation of the nanoshells presents several alternative sensing options, the opportunity exists to build redundancies into the monitoring system to either simplify or accelerate the signal analysis following data acquisition.

One type of glucose sensing system includes first assessing in vitro the Raman signals from glucose, to determine the SERS enhancements obtained with resonant nanoshells under "ideal" conditions. Binding assays with bicinchoninic acid (BCA) assays of bioconjugate nanoshells are then performed to evaluate total protein adsorbed and absolute activities. Raman studies of in vitro glucose monitoring with bioconjugate nanoshells are then performed to evaluate the sensitivity to reactant, adsorbate and product species. The next step is to embed nanoshells into glucose permeable hydrogels such as polyethylene glycol diacrylate (PEGDA), polyvinyl alcohol or alginate, adapting a known technique or chemical protocol for embedding spheres in hydrogels. In vivo demonstration of the biosensing system may include Raman studies of diabetic and non-diabetic rats with subcutaneously implanted nanoshell-based sensors and correlation of the optically measured glucose levels with traditionally measured blood glucose levels. For example, a group of SDD (genetically diabetic) rats may be injected subcutaneously, at a site in the body where glucose sensing is desired, with an appropriate quantity of suitably designed nanoshells in a non-interfering pharmacologically acceptable carrier. Alternatively, the injectate could comprise hydrogel forming material such as 0.1 ml of 20% w/v PEGDA with 1 $\mu$m eosin Y in sterile physiological saline containing bioconjugate nanoshells. The conjugated biomolecule could be one that interacts with glucose in such a way that a Raman active spectral feature is provided. A suitable Raman active reporter molecule could be employed, if desired. After injection of the hydrogel precursors, rapid photopolymerization (<5 sec) is achieved in situ by exposure to light from a Xe arc lamp. This process can be safely carried out in direct contact with cells and tissues without observable damage. Subsequently (e.g., beginning on the third post-operative day), measurement of the glucose level at the site of hydrogel implantation is made by Raman spectroscopy. Simultaneously, blood may be withdrawn from each animal for monitoring of blood glucose level by conventional techniques. The Raman signal is correlated to a glucose level and can be confirmed by comparison to the blood glucose level in the diabetic and normoglycemic rats obtained using conventional techniques.

Although a direct glucose sensing method and a method employing bioconjugation of glucose oxidase enzyme for glucose sensing are described in the foregoing example, one can readily appreciate that other chemicals or analytes may be monitored similarly and other proteins or biomolecules may be similarly adsorbed to other nanoshells with suitable core:shell design and optical properties. The present example describes preferred in vivo biosensing techniques employing near-infrared range radiation. Although less preferred than near-infrared range excitation and detection methods, for many applications visible or UV range radiation may be used instead, along with appropriately designed nanoshells that demonstrate SERS in the visible or UV range, and can provide satisfactory spectroscopic measurements.

EXAMPLE 5

Nanoshell-based Immunosorbent Assays (NISA)

Bioconjugate nanoshells are expected to contribute significantly to the streamlining of a variety of immunoassay processes. Nanoshell-based immunosorbant assays provide all-optical bioassays that can be used to replace ELISA-type assays, for example. The analytical technique of enzyme-linked immunoadsorbant assay (ELISA) and related techniques are now the most widely known immunoassays. A vast number of commercial ELISA-based assays are available for detection of antibodies (autoantibodies, antiviral or antibacterial antibodies) or antigens (serum proteins, cytokines, hormones, drugs, etc.) (M. A. Kerr, et al., eds. Immunochemistry Labfax BIOS Scientific Publishers, Ltd., Oxford, U.K. 1994). They allow detection of antibodies or antigens with considerable accuracy and sensitivity. The stages of a conventional ELISA procedure generally include initially adsorbing an antibody onto a solid support. Upon incubation with a plasma sample an antibody-target protein complex is formed. The final sandwich immunoassay complex typically includes an indicator enzyme that permits optical measurements of the antigen concentration. These assays are usually carried out in flat-bottomed microtitration well strips or plates and require several hours to perform. Since the final detection involves monitoring of an optical signal (usually a color change or fluorescence of the final sandwich complex) this places certain constraints on sample preparation. For instance, the solution must be highly transparent in the visible region where the color change would be detected. Because cell membrane interferes with protein adsorption in the assay, the samples need to be acellular, so blood samples must be processed to plasma. Conventional ELISA-type techniques tend to be highly time-consuming, and are therefore underutilized in the clinical setting, where long time delays in obtaining test results are problematic.

Figure 8C:
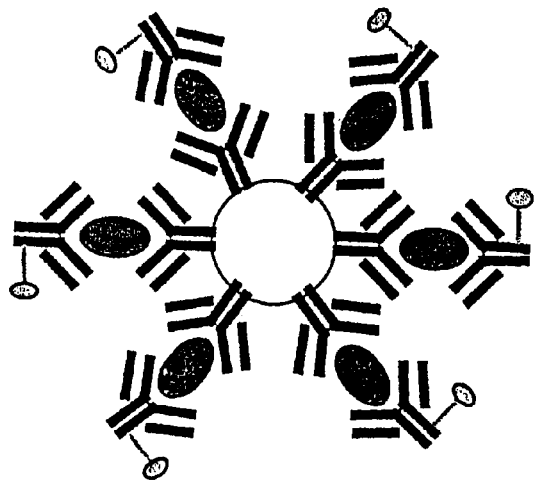
FIGS. 8A–C conceptually illustrate an ELISA test that is modified by directly linking the initial antibodies to nanoshells instead of attaching to a typical macroscopic support.
Figure 8B:
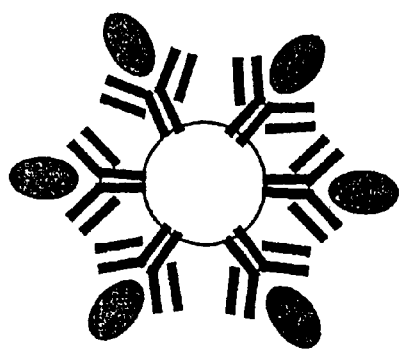
Figure 8A:
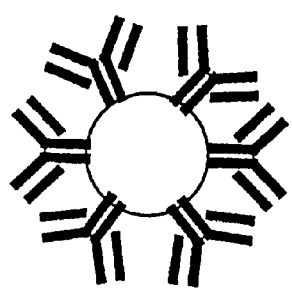

In a nanoshell-modified ELISA process, for example, instead of attaching the initial antibodies to a macroscopic support, they are instead directly linked to suitably designed nanoshells, as shown in FIG. 8A. FIG. 8A is a conceptual illustration of an antibody-nanoshell conjugate prior to assay. As in the case of the glucose sensor described above, the nanoshells are fabricated such that their plasmon resonance corresponds to the Raman near-infrared excitation wavelength, providing SERS enhancements to the resulting spectra. This permits analysis and/or detection in samples of whole blood. The bioconjugated nanoshells are prepared with precisely known concentrations of specific active antibody species attached to their surfaces, quantified using a binding assay with a BCA assay. These bioconjugated nanoshells are then added to a fluid sample containing the analyte, forming antibody-target protein complexes as shown in FIG. 8B. Both before and after the analyte has bound to the antibodies, the Raman spectra under near infrared excitation is monitored. Both of these stages are expected to yield SERS-enhanced Raman signals and present the opportunity for quantitative analysis. FIG. 8C shows a nanoshell analog of a sandwich immunoassay, i.e., attachment of a conjugated antibody to the antibody-target protein complex. When nanoshells are employed, the "sandwich" step is nonessential, yet provides redundancy of information that may be particularly useful for confirmation or calibration of a technique. Biosensing with nanoshells may be accomplished with any of the configurations depicted in FIGS. 8A–C.

Another type of nanoshell-based in vitro immunoassay includes conjugating a complex mixture of biomolecules to a nanoshell surface. The biomolecule mixture contains a specific antigen of interest. An appropriate antibody having affinity for binding to the antigen is then used as a probe for the presence of the antigen-antibody complex by SERS. The antibody is labeled with a reporter molecule or dye that exhibits a large Raman cross-section, such as dimethylaminoazobenzene (DAB) or rhodamine.

As in the case of in vivo sensing of biological analytes, there are also significant advantages in using near infrared Raman spectroscopy for in vitro assay techniques. In protein adsorption based assays, cells interfere with the desired binding and produce erratic responses. This necessitates extra time-consuming separation and purification steps in sample preparation prior to the bioassay. A near infrared Raman-based bioassay probes these samples in a spectral region of high transmissivity, eliminating much of the need for time-consuming sample preparation.

EXAMPLE 6

Non-interference of Plasma Proteins in Nanoshell SERS

One important advantage of employing nanoshell SERS for in vitro assays is that interference with the near-IR SERS signal due to extraneous proteins in the biological sample can be avoided by employing appropriately designed nanoshells or conjugated nanoshells. This was demonstrated by subjecting samples of dimethylaminoazobenzene labeled-IgG (DAB-IgG) conjugated nanoshells suspended in either phosphate buffered saline (PBS), fetal bovine serum (FBS), or whole blood to near-infrared radiation using a 1064 nm Nd:YAG (pulse) laser system. The near-infrared SERS signal of each sample was measured and the results are shown in FIGS. 9A–C. FIG. 9A shows the measured Raman intensity vs Raman shift ($cm^{-1}$) for the sample suspended in PBS. FIGS. 9B and 9C show the results obtained with like samples of DAB-IgG conjugated nanoshells suspended in FBS and whole blood, respectively. It was observed that serum proteins do not interfere with the near-IR SERS signal (FIG. 9B) and that very little attenuation of the signal was observed in whole blood (FIG. 9C). The nanoshells had an approximately 200 nm diameter $SiO_2$ core, an approximately 10 nm thick gold shell and a diameter of about 110 nm (SD±about 10%). The maximum absorbance wavelength of one group of $Ag/SiO_2$ particles was optically tuned to approximately match the 1064 mn (peak) laser wavelength (±10–15 nm, preferably no more than about 10 nm off peak). Conjugation of the DAB-Ig was accomplished using a procedure similar to that described above for conjugating glucose oxidase to nanoshells.

The Raman spectroscopy based in vitro bioassay will allow very rapid quantification of plasma proteins including antibodies (such as anti-viral or anti-bacterial antibodies), cytokines or drugs. This technique is expected to be significantly simpler than conventional bioassays such as the ELISA or radioimmunoassay. In this new kind of bioassay, whole blood (either in a smear from a single drop or in a test tube) is incubated with the appropriate bioconjugate nanoshells, then immediately analyzed via Raman spectroscopy. Accurate bioassay results may be obtained in minutes rather than, typically, 24–48 hours. Although initial attachment of an antibody to the nanoshells is described in the foregoing example, in many alternative immunoassays an antigen instead of an antibody may be linked to the nanoshell initially.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is limited only by the claims which follow, that scope including all equivalents of the subject matter of the claims. The disclosures of all patents, patent documents, and publications cited herein are incorporated by reference to the extent that they describe pertinent materials or methods not explicitly set forth herein.

What is claimed is:

1. A chemical sensing device comprising a plurality of particles, each said particle comprising:

a non-conducting core having an independently defined radius;

a metal shell linked to said core by a linker molecule and having an independently defined thickness, a defined core radius:shell thickness ratio;

a defined absorbance or scattering wavelength maximum in the ultraviolet to infrared range, said defined wavelength substantially matched to a wavelength of a predetermined source of electromagnetic radiation;

a surface for inducing surface enhanced Raman scattering;

optionally, at least one biomolecule conjugated to said surface;

optionally, a reporter molecule conjugated to said shell or said biomolecule, wherein said particle is made according to a method comprising:
providing said non-conducting core;
binding at least one linker molecule to said core;

binding metal molecules to said linker molecules to form a discontinuous metal colloid layer; and reducing additional metal molecules onto the discontinuous metal colloid layer so as to form said metal shell, wherein said shell surrounds said non-conducting core such that said wavelength maximum varies according to the thickness of said shell.

2. The device of claim 1 further comprising a support.

3. The device of claim 2 wherein said support comprises a medium that is permeable to an analyte of interest.

4. The device of claim 3 wherein said medium comprises a matrix.

5. The device of claim 2 wherein said particles are arrayed on said support.

6. The device of claim 4 wherein said medium is chosen from the group consisting of hydrogels, protein gels and polymers.

7. The device of claim 1 wherein said surface or said biomolecule conjugated to said surface has an affinity for an analyte of interest.

8. The device of claim 2 wherein said support, or a portion thereof, has an affinity for an analyte of interest.

9. The device of claim 7 wherein said surface or said biomolecule conjugated to said surface has an affinity for said analyte molecule to localize said analyte molecule to within about 100 nm of said surface.

10. The device of claim 1 wherein said defined wavelength absorbance or scattering maximum is in the near-infrared range of the electromagnetic spectrum.

11. The device of claim 1 wherein said particle has an absorbance or scattering wavelength maximum of about 800–1,300 nm or about 1,600–1,850 nm.

12. The device of claim 1 wherein said biomolecule is selected from the group consisting of proteins, polypeptides, oligonucleotides and polysaccharides.

13. The device of claim 1 wherein said biomolecule is glucose oxidase and said analyte is glucose.

14. The device of claim 1 wherein said biomolecule is an antibody and said analyte is a target antigen for said antibody.

15. The device of claim 1 wherein said shell comprises a metal selected from the group consisting of gold and silver.

16. The device of claim 1 wherein said core comprises a material selected from the group consisting of silicon dioxide, gold sulfide, titanium dioxide, polymethyl methacrylate (PMMA), polystyrene and dendrimers.

17. The device of claim 16 wherein said core comprises silicon dioxide and said shell comprises gold.

18. The device of claim 16 wherein said core comprises gold sulfide and said shell comprises gold.

19. The device of claim 1 wherein said particle has a diameter up to about 5 $\mu$m, a core diameter of about 1 nm to less than about 5 $\mu$m, a shell thickness of about 1–100 nm.

20. The device of claim 19 wherein said core is about 1 nm–2 $\mu$m in diameter, said shell is less than about 40 nm thick and is linked to said core by a linker molecule, and said particle has an absorbance wavelength maximum between 300 nm and 20 $\mu$m.

21. The device of claim 20 wherein said particle has a diameter of about 210 nm, has a $SiO_2$ core with a radius of about 100 nm, a gold shell about 10 nm thick, a core radius:shell thickness of about 10:1, and a maximum absorbance wavelength ($\lambda_{max}$) of about 1064 (SD±10 nm).

22. A kit for conducting a nanoshell-based immunosorbent assay, said kit comprising:

a quantity of a first antibody-nanoshell conjugate;

optionally, a quantity of a control antigen having affinity for binding to said first antibody;

optionally, a quantity of a secondary antibody having affinity for binding to an antigen-first antibody-nanoshell conjugate, and optionally, a reporter molecule bound to said secondary antibody, said reporter molecule containing a Raman active functional group, each said nanoshell comprising:

a non-conducting core having an independently defined radius, a metal shell linked to said core by a linker molecule and having an independently defined thickness, a defined core radius:shell thickness ratio, a defined absorbance wavelength maximum in the ultraviolet to infrared range of the electromagnetic spectrum, and a surface for inducing surface enhanced Raman scattering, wherein said nanoshell is made according to a method comprising:

providing said non-conducting core;

binding at least one linker molecule to said core;

binding metal molecules to said linker molecules to form a discontinuous metal colloid layer; and reducing additional metal molecules onto the discontinuous metal colloid layer so as to form said metal shell, wherein said shell surrounds said non-conducting core such that said wavelength maximum varies according to the thickness of said shell.

23. The kit of claim 22 wherein said assay is a sandwich-type immunosorbent assay.

24. The kit of claim 22 wherein said assay is a direct-type immunosorbent assay.

25. The kit of claim 22 wherein said assay is an indirect-type immunosorbent assay.

* * * * *